Figure 1:
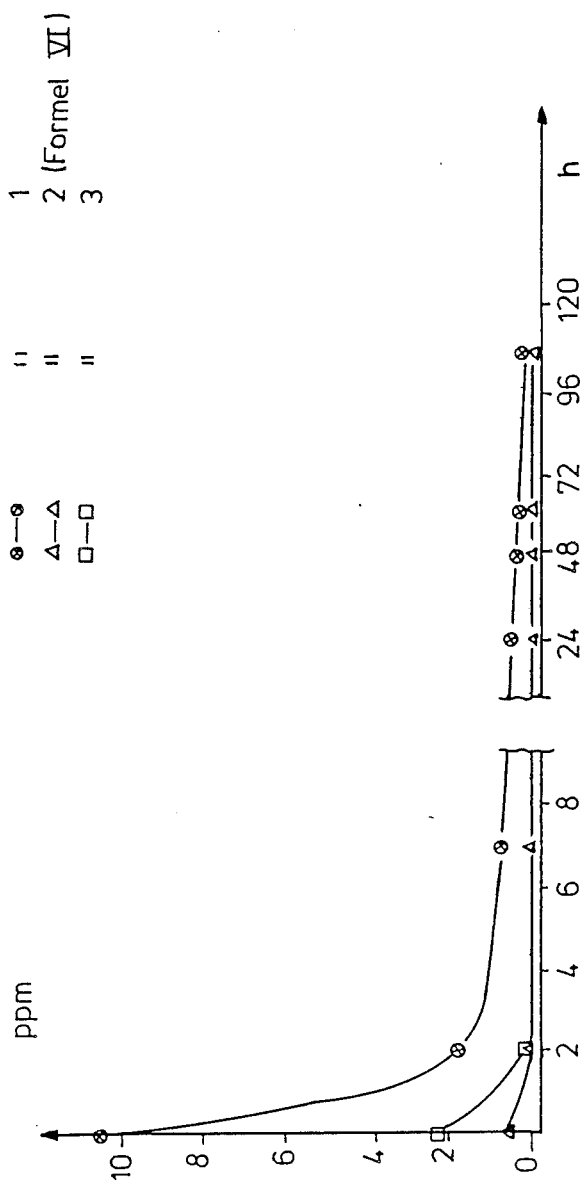

United States Patent [19]

Preiss et al.

[11] Patent Number: 4,973,590
[45] Date of Patent: Nov. 27, 1990

[54] PROCESS FOR THE PREPARATION OF QUINOLONECARBOXYLIC ACIDS WHICH CAN BE ADMINISTERED PARENTERALLY

[75] Inventors: Michael Preiss, Wuppertal; Ulrich Schorsch, Duesseldorf; Arthur Haaf, Wuppertal; Paul Naab, Elkhart; Rudolf Zerbes, Wuppertal, all of Fed. Rep. of Germany

[73] Assignee: Bayer Aktiengesellschaft, Leverkusen, Fed. Rep. of Germany

[21] Appl. No.: 181,809

[22] Filed: Apr. 15, 1988

[30] Foreign Application Priority Data

Apr. 24, 1987 [DE] Fed. Rep. of Germany ....... 3713672

[51] Int. Cl.$^5$ ................ C07D 401/04; A61K 31/495
[52] U.S. Cl. .................. 514/254; 514/224.5; 514/228.2; 514/228.5; 514/230.2; 514/233.2; 514/233.5; 514/234.5; 514/294; 514/300; 514/312; 544/60; 544/61; 544/62; 544/126; 544/127; 544/128; 544/349; 544/363; 546/122; 546/123; 546/156
[58] Field of Search ............... 514/312, 254; 544/363; 546/156

[56] References Cited

U.S. PATENT DOCUMENTS

| | | | |
|---|---|---|---|
| 4,292,317 | 9/1981 | Pesson | 544/128 |
| 4,616,019 | 10/1986 | Chu | 514/254 |
| 4,638,067 | 1/1987 | Culbertson et al. | 544/363 |
| 4,705,789 | 11/1987 | Grohe et al. | 544/362 |

FOREIGN PATENT DOCUMENTS 3420116 12/1985 Fed. Rep. of Germany ...... 514/254
2498931 6/1982 France.

OTHER PUBLICATIONS

*Fundamentals of Analytical Chemistry*, (3rd. Ed.), by Skoog and West, pp. 7, 127–130 (1976).

Primary Examiner—Mukund J. Shah
Assistant Examiner—E. Bernhardt
Attorney, Agent, or Firm—Sprung Horn Kramer & Woods

[57] ABSTRACT

Known quinolone carboxylic acid derivatives of the formula

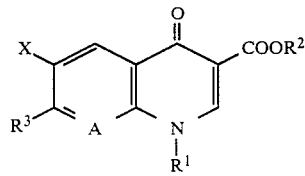

are treated so as to become readily administrable parenterally, the treatment comprising dissolving the active compound using an acid, allowing the solution to stand for about 0.15 to 150 hours at a temperature from room temperature to the boiling point of the solution, filtering the solution, precipitating the active compound from the solution using a basic reagent, and converting the precipitated active compound into a form which can be administered parenterally.

2 Claims, 1 Drawing Sheet

PROCESS FOR THE PREPARATION OF QUINOLONECARBOXYLIC ACIDS WHICH CAN BE ADMINISTERED PARENTERALLY

The invention relates to a new process for the preparation of quinolonecarboxylic acids which are suitable for the production of solutions which can be administered parenterally.

Very pure quinolonecarboxylic acids are already produced in the synthesis. However, these are not suitable for the production of injection and infusion solutions since the latter are not stable on storage. Precipitation occurs after some time, rendering the solutions unusable.

Quinolonecarboxylic acids from which solutions which are stable on storage can be produced have not been successfully obtained by any of the processes investigated hitherto, for example by reprecipitation or recrystallization.

The invention relates to quinolonecarboxylic acid solutions which can be administered parenterally and which are characterized in that they contain quinolonecarboxylic acids, or derivatives thereof, of the general formula (I)

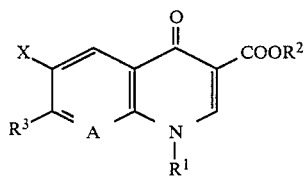

in which
$R^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl,
$R^2$ represents hydrogen, alkyl having 1 to 4 carbon atoms or (5-methyl-2-oxo-1,3-dioxol-4-yl)-mehtyl,
$R^3$ represents methyl or a cyclic amino group, such as

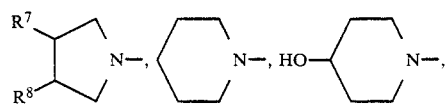

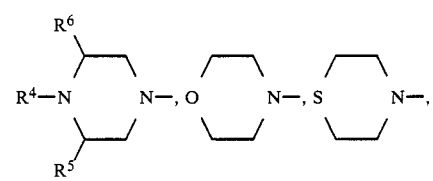

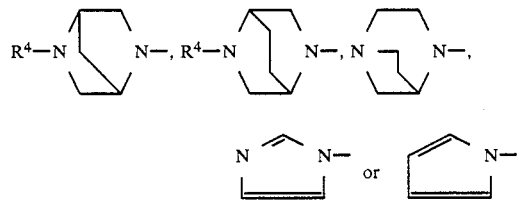

in which
$R^4$ represents hydrogen, alkyl having 1 to 4 carbon atoms, 2-hydroxyethyl, allyl, propargyl, 2-oxopropyl, 3-oxobutyl, phenacyl, formyl, $CFCl_2-S-$, $CFCl_2-SO_2-$, $CH_3O-CO-S-$, benzyl, 4-aminobenzyl or

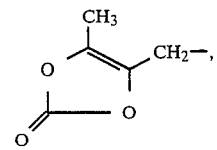

$R^5$ represents hydrogen or methyl,
$R^6$ represents hydrogen, alkyl having 1 to 4 carbon atoms, phenyl or benzyloxymethyl,
$R^7$ represents hydrogen, amino, methylamino, ethylamino, aminomethyl, methylaminomethyl, ethylaminomethyl, dimethylaminomethyl, hydroxyl or hydroxymethyl,
$R^8$ represents hydrogen, methyl, ethyl or chlorine,
X represents fluorine, chlorine or nitro, and
A represents N or C—$R^9$, in which
$R^9$ represents hydrogen, halogen, such as fluorine or chlorine, methyl or nitro, or alternatively, together with $R^1$, can form a bridge of the structure

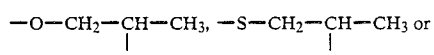

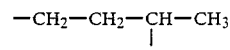

in dissolved form with no more than 1 to 10 ppm, preferably 1 to 5 ppm, relative to the major active compound component of the solution, of secondary components.

The invention relates to a process in which quinolonecarboxylic acids which are already very pure are subjected to specific treatment, so that solutions which are stable on storage can be produced therefrom.

In particular, the invention relates to a process for the production of quinolonecarboxylic acid solutions which can be administered parenterally and which contain quinolonecarboxylic acids, or derivatives thereof, of the general formula (I)

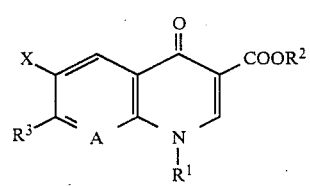

in which
$R^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl,
$R^2$ represents hydrogen, alkyl having 1 to 4 carbon atoms or (5-methyl-2-oxo-1,3-dioxol-4-yl)-methyl,
$R^3$ represents methyl or a cyclic amino group, such as

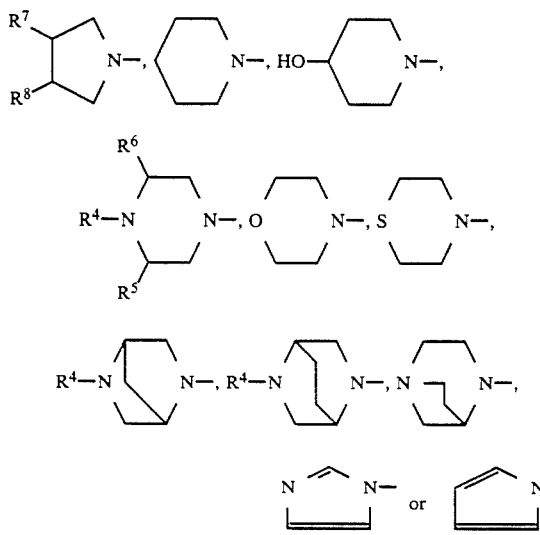

in which

R[4] represents hydrogen, alkyl having 1 to 4 carbon atoms, 2-hydroxyethyl, allyl, propargyl, 2-oxopropyl, 3-oxobutyl, phenacyl, formyl, $CFCl_2-S-$, $CFCl_2-SO_2-$, $CH_3O-CO-S-$, benzyl, 4-aminobenzyl or

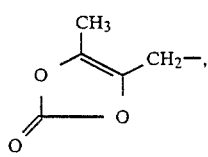

R[5] represents hydrogen or methyl,
R[6] represents hydrogen, alkyl having 1 to 4 carbon atoms, phenyl or benzyloxymethyl,
R[7] represents hydrogen, amino, methylamino, ethylamino, aminomethyl, methylaminomethyl, ethylaminomethyl, dimethylaminomethyl, hydroxyl or hydroxymethyl,
R[8] represents hydrogen, methyl, ethyl or chlorine,
X represents fluorine, chlorine or nitro, and
A represents N or $C-R^9$, in which
  R[9] represents hydrogen, halogen, such as fluorine or chlorine, methyl or nitro, or alternatively, together with R[1], can form a bridge of the structure

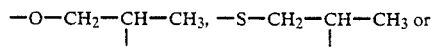

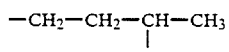

in dissolved form with no more than 1 to 10 ppm, preferably 1 to 5 ppm, relative to the major active compound component of the solution, of secondary components, characterized in that an active compound of the formula I is dissolved using acid, the solution is allowed to stand, if appropriate with stirring, for 0.15 to 150 hours, preferably 0.25 to 110 hours, at temperatures from room temperature to the boiling point of the solution, if appropriate in the presence of activated charcoal, the solution is filtered, the quinolonecarboxylic acid is precipitated using basic reagents, and the precipitated quinolonecarboxylic acid is converted using conventional auxiliaries, into an administration form which can be administered parenterally.

The process according to the invention preferably has the form that the active compounds used are those of the general formula (I) in which R[3] represents the

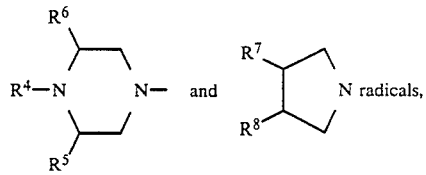

in which R[4], R[5], R[6], R[7] and R[8] have the abovementioned meaning.

The process according to the invention is particularly preferably carried out in a fashion where the active compounds used are those of the general formula I in which X represents fluorine or chlorine and A represents CH, C—Cl, C—F or C—Br, or in the fashion where the active compounds used are those of the general formula I in which X represents fluorine and A represents CH, C—Cl or CF, and R[3] denotes the

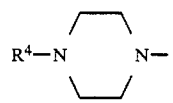

radical where $R_4$=H, $C_2H_5$, $CH_3$ or $-CH_2-CH_2-OH$ or the

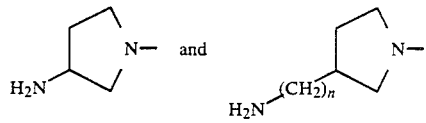

radicals where n=1 to 4.

The process includes storage at room temperature to the boiling point of the solution in the presence of activated charcoal, or alternatively without activated charcoal, of solutions, saturated at the particular temperature, of the compounds of the formula I containing hydrochloric acid, and standing times from 0.15 to 150, preferably 0.25 to 110, hours. Suitable filtration auxiliaries are, for example, a very wide variety of types of kieselguhr. Similarly, a very wide variety of types of charcoal can be employed. The basic agents used for precipitation can be alkali metal hydroxides, alkaline-earth metal hydroxides, ammonia or organic bases, such as, for example, tertiary amines.

The process according to the invention is carried out, for example, by dissolving the quinolonecarboxylic acid itself or in the form of its salts, if appropriate with addition of acid, in water or other suitable solvents at temperatures from room temperature to the boiling point of the solvent until saturation is achieved. The remaining measures follow after dissolution.

Suitable acids are: an amount, sufficient for dissolution of the active compounds, of one or more acid(s) mixed with water, from the group comprising hydrochloric acid, methanesulphonic acid, propionic acid, succinic acid, glutaric acid, citric acid, fumaric acid, maleic acid, tartaric acid, glutaminic acid, gluconic acid, glucuronic acid, galacturonic acid, ascorbic acid, phosphoric acid, adipic acid, hydroxyacetic acid, sulphuric acid, nitric acid, acetic acid, malic acid, L-aspartic acid and lactic acid.

Lactic acid and hydrochloric acid, or mixtures of lactic acid and hydrochloric acid, are particularly preferred.

The amounts can be determined by simple smallscale experiments.

The active compounds purified according to the invention can be added directly or processed into infusion solutions etc. according to the teaching of EP Nos. 138,018-A3 and 86,114,131.5.

The very particularly preferred active compound used in the process according to the invention is ciprofloxacin.

In an expedient manner, saturated ciprofloxacin solutions containing hydrochloric acid are allowed to stand at the particular temperature for 0.15 to 150 hours, activated charcoal being employed.

The invention furthermore relates to solutions or active compounds which are prepared by the process according to the claims for use in a process for therapeutic treatment of the human or animal body.

The invention likewise relates to the use, for the production of medicaments, of solutions or active compounds which have been prepared by the processes according to the invention.

It can be described as extremely unexpected that through storage of the solutions, containing hydrochloric acid, of the quinolonecarboxylic acids of the formula I′

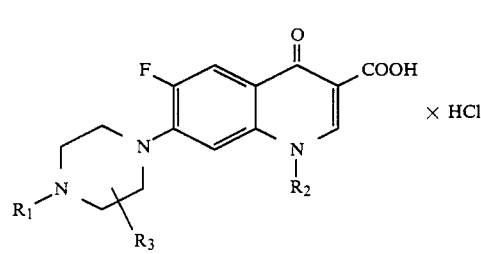

over a certain period of time in the presence of activated charcoal, or alternatively without activated charcoal, filtration of the solutions containing hydrochloric acid with or without the use of filtration auxiliaries and subsequent precipitation using basic media, quinolonecarboxylic acids are obtained whose solutions are stable on storage. The quinolonecarboxylic acids exist as betaines whose structure can be represented as shown in the formula II

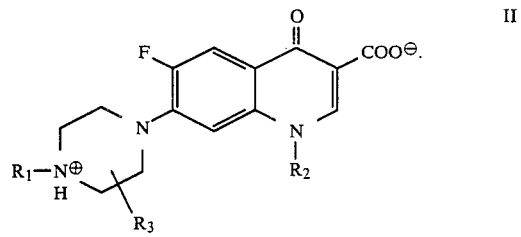

The deposits are probably attributable to sparingly soluble polycondensation products which have a very low crystal-growth rate. Caused by the low crystal-growth rate, such compounds cause supersaturated solutions which flocculate after an uncertain time.

Thus, for example, it was possible to detect compounds of the general formula IV

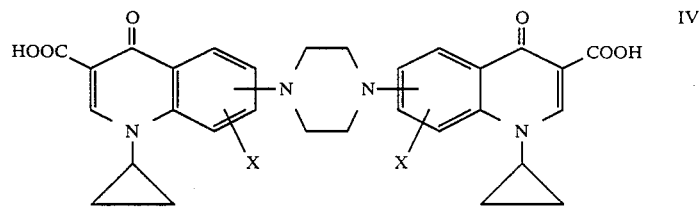

in the ppm region in solutions of compound III

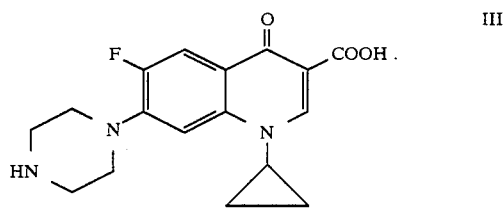

Through the process described, the amounts of the compounds of the formula IV, of which compound VI may be mentioned, for example,

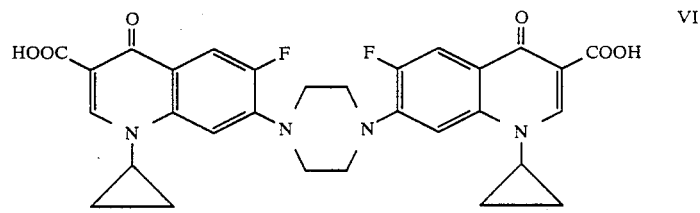

can be reduced so that solutions of compound III which are stable on storage are obtained.

Other processes for removing these extremely low proportions of compounds of the general formula IV have not been successful. Thus, it has not been possible to remove the above by-products through recrystallization of compounds of the formula I or corresponding salts. Reprecipitation of the compounds of the formula I in an alkaline medium likewise brought no usable result, nor did the addition of a very wide variety of solvents.

The invention will be further described with reference to the accompanying drawing, wherein the FIGURE shows particle-relevant by-products for the active compound ciprofloxacin. By-products 1, 2 and 3 are shown here as examples. The structure of by-product 2 is reproduced in formula VI.

EXAMPLE 1

30 parts by weight of ciprofloxacin hydrochloride and 3 parts by weight of activated charcoal are stirred for 2 hours in 1,080 parts by weight of water. The mixture is then filtered, and the pH is adjusted to 7.8 using potassium hydroxide solution. The precipitate is separated off, washed and dried. Yield: 22 parts by weight of ciprofloxacin.

EXAMPLE 2

As for Example 1; however the reaction time is 48 hours.

EXAMPLE 3

As for Example 1; however, the reaction time is 108 hours.

EXAMPLE 4

As for Example 1; sodium hydroxide solution is employed in place of potassium hydroxide solution.

EXAMPLE 5

As for Example 2; aqueous ammonia is employed in place of potassium hydroxide solution.

EXAMPLE 6

As for Example 3; triethylamine is employed in place of potassium hydroxide solution.

EXAMPLE 7

41 parts by weight of ciprofloxacin hydrochloride and 4.1 parts by weight of activated charcoal are stirred for 60 hours at 30° C. in 700 parts by weight of water. Work-up takes place as in Example 1. Yield: 31.6 parts by weight of ciprofloxacin.

EXAMPLE 8

82 parts by weight of ciprofloxacin hydrochloride and 8.2 parts by weight of activated charcoal are stirred for 60 hours at 50° C. in 700 parts by weight of water. Work-up takes place as in Example 1. Yield: 65.7 parts by weight of ciprofloxacin.

EXAMPLE 9

As for Example 1; 3 parts by weight of kieselguhr are employed in place of activated charcoal.

EXAMPLE 10

As for Example 1; 1.5 parts by weight of activated charcoal and 1.5 parts by weight of kieselguhr are employed.

EXAMPLE 11

As for Example 1; but without activated charcoal.

EXAMPLE 12

As for Example 8; but without activated charcoal.

It will be appreciated that the instant specification and claims are set forth by way of illustration and not limitation, and that various modifications and changes may be made without departing from the spirit and scope of the present invention.

What is claimed is:

1. A process for the production of ciprofloxacin in a form which can be administered parenterally, comprising forming a saturated solution of a salt of ciprofloxacin with hydrochloric acid, adding activated charcoal to the solution, allowing the solution to stand for about 0.25 to 110 hours at a temperature from room temperature to the boiling point of the solution, filtering the solution, precipitating the active compound from the solution using a basic reagent selected from the group consisting of alkali metal hydroxides, alkaline earth metal hydroxides, ammonia and tertiary amines, and dissolving the precipitated active compound.

2. A parenterally administrable solution of the product produced by the process of claim 1.

* * * * *

UNITED STATES PATENT AND TRADEMARK OFFICE
CERTIFICATE OF CORRECTION

PATENT NO. : 4,973,590

DATED : November 27, 1990

INVENTOR(S) : Preiss et al.

It is certified that error appears in the above-identified patent and that said Letters Patent is hereby corrected as shown below:

Title Page   [75] Inventors:   3rd line after " Wuppertal " insert -- all of Fed. Rep. of Germany -- and after " Elkhart " insert --Indiana--   4th line delete " all of "

Signed and Sealed this

Tenth Day of November, 1992

Attest:

DOUGLAS B. COMER

*Attesting Officer*   Acting Commissioner of Patents and Trademarks